United States Patent [19]

Gray

[11] 4,420,322

[45] Dec. 13, 1983

[54] HERBICIDAL ANTIDOTES

[75] Inventor: Reed A. Gray, Saratoga, Calif.

[73] Assignee: Stauffer Chemical Company, Westport, Conn.

[21] Appl. No.: 26,112

[22] Filed: Apr. 2, 1979

[51] Int. Cl.³ .............................................. A01N 25/32
[52] U.S. Cl. ............................................ 71/82; 71/83
[58] Field of Search ...................................... 71/82, 83

[56] References Cited

U.S. PATENT DOCUMENTS

| 2,913,327 | 11/1959 | Tilles et al. | 71/100 |
| 3,185,720 | 5/1965 | Tilles et al. | 260/455 |
| 3,198,786 | 8/1965 | Tilles et al. | 260/239 |
| 3,874,868 | 1/1975 | Chandler | 71/65 |
| 3,880,646 | 4/1975 | Connell et al. | 71/111 |

Primary Examiner—Catherine L. Mills
Attorney, Agent, or Firm—Harry A. Pacini

[57] ABSTRACT

This invention describes herbicidal compositions comprised of a thiocarbamate or an acetanilide herbicide and an antidotally effective amount of an alkali azide salt or an alkaline earth salt.

7 Claims, No Drawings

HERBICIDAL ANTIDOTES

BACKGROUND OF THE INVENTION

Uses of Herbicides

An herbicide is a compound which controls or modifies plant growth, e.g., killing, retarding, defoliating, desiccating, regulating, stunting, tillering, stimulating, and dwarfing. "Plant" refers to all physical parts, including seeds, seedlings, saplings, roots, tubers, stems, stalks, foliage, and fruits. "Plant growth" is meant to include all phases of development from seed germination to natural or induced cessation of life.

Herbicides are generally used to control or eradicate weed pests. They have gained a high degree of commercial success because it has been shown that such control increases crop yield and reduces harvesting costs.

Herbicidal effectiveness is dependent upon several variables. One of these is the time or growth related method of application. The most popular methods of application include: pre-plant incorporation into the soil; pre-emergence surface treatment of seeded soil; and post-emergence treatment of the plant and soil.

The most important determinant of herbicidal effectiveness is the susceptibility of the target weed. Certain herbicidal compounds are phytotoxic to some weed species but not to others.

The manufacturer of the herbicide recommends a range of rates and concentrations calculated to maximize weed control. The range of rates varies from approximately 0.01 to 50 pounds per acre, usually from 0.1 to 25 pounds per acre. The actual amount used depends upon several considerations including particular weed susceptiblity and overall cost limitations.

Need for Herbicidal Antidotes

Unfortunately, few herbicides are selective exclusively of weed species. Many are toxic to both weeds and the intended crop beneficiary. Therefore, a particular herbicide's use may be proscribed by its injurious effect on the cultivated crop even though it may otherwise provide excellent control of weeds plaguing that crop.

To preserve the beneficial aspects of herbicide use and to mitigate crop damage, many herbicidal antidotes have been prepared. These antidotes reduce or eliminate damage to the crop without substantially impairing the ameliorative effect of the herbicide. See U.S. Pat. No. 4,021,224 and Belgian Pat. No. 846,894.

Although several explanatory theories have been advanced, the precise mechanism by which an antidote reduces herbicidal injury has not been empirically verified. An antidote compound may in fact be a remedy, interferent, protectant, antagonist, or inhibitor. As used herein "antidote" describes the effect of herbicidal phytotoxicity to weed species and reduced or non-phytotoxicity to cultivated crop species.

SUMMARY

It has been discovered that the tolerances of cultivated crops to thiocarbamate and actanilide herbicides can be increased by addition of a small amount of an alkali azide salt or an alkaline earth azide salt.

DESCRIPTION OF THE INVENTION

Alkali azide salts may include an element selected from lithium, sodium, potassium, rubidium, cesium, and ammonium. Alkaline earth azide salts may include the elements selected from calcium and barium.

Sodium azide salt was used to test the compositions and methods of this invention. Other alkali azide salts or alkaline earth azide salts, especially potassium, ammonium, and calcium, could have been used equally well. Therefore, this invention consists of a herbicidal composition comprised of (a) a herbicidally effective amount of a thiocarbamate of the formula

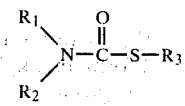

in which $R_1$ is selected from the group consisting of 1 to 6 carbon alkyl and 2 to 6 carbon alkenyl;

$R_2$ is selected from the group consisting of 1 to 6 carbon alkyl, 2 to 6 carbon alkenyl, cyclohexyl and phenyl; or $R_1$ and $R_2$ taken together with the nitrogen atom to which they are attached form an alkylene ring; and $R_3$ is selected from the group consisting of 1 to 6 carbon alkyl, 1 to 6 carbon haloalkyl, 5 to 10 carbon alkylene ring, phenyl and benzyl; and (b) an antidotally effective amount of an alkali azide or alkaline earth azide salt.

This invention also consists of (a) an herbicidally effective amount of an acetanilide of the formula

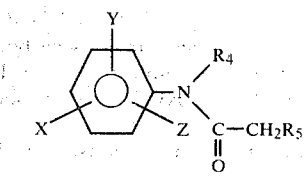

in which

X, Y, and Z are independently selected from the group consisting of hydrogen and 1-4 carbon alkyl.

$R_4$ is selected from the group consisting of 1-6 carbon alkyl, 2-10 carbon alkylalkoxy, 2-6 carbon acetoxy, and dioxane; and $R_5$ is selected from the group consisting of chlorine, bromine, and iodine; and (b) an antidotally effective amount of an alkali azide or alkaline earth azide salt.

The terms "alkyl" and "alkenyl" as used herein are intended to include both straight and branched chain groups. All carbon atom ranges are intended to be inclusive of both upper and lower limits.

The thiocarbamates have been shown particularly effective in the control of grassy type weeds which interfere with the cultivation of a wide variety of crops, e.g., barley, corn, lentils, peanuts, peas, potatoes, soybeans, spinach, tobacco and tomatoes. The herbicidal activity of the acetanilides is similar to that of the thiocarbamates.

This invention also includes the method of protecting crops while maintaining effective weed control by the addition to the soil of (a) an herbicidally effective amount of a thiocarbamate of the formula

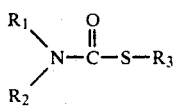

in which

R₁ is selected from the group consisting of 1 to 6 carbon alkyl and 2 to 6 carbon alkenyl;

R₂ is selected from the group consisting of 1 to 6 carbon alkyl, 2 1 to 6 carbon alkenyl, cyclohexyl and phenyl; or R₁ and R₂ taken together with the nitrogem atom to which they are attached form an alkylene ring; and R₃ is selected from the group consisting of 1 to 6 carbon alkyl, 1 to 6 carbon haloalkyl, 5 to 10 carbon alkylene ring, phenyl and benzyl; and (b) an antidotally effective amount of an alkali azide or alkaline earth azide salt.

The invention also embodies the method of protecting crops from acetanilide herbicidal injury whi ch comprises adding to the soil (a) an herbicidally effective amount of an acetanilide of the formula

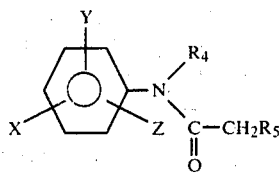

in which

X, Y, and Z are independently selected from the group consisting of hydrogen and 1-4 carbon alkyl;

R₄ is selected from the group consisting of 1-6 carbon alkyl, 2-10 carbon alkylalkoxy, 2-6 carbon acetoxy, and dioxane; and R₅ is selected from the group consisting of chlorine, bromine and iodine; and (b) an antidotally effective amount of an alkali azide or alkaline earth azide salt.

The most efficacious method of applying the herbicidal composition of this invention is by post-emergence "herbigation." See "Herbigation: Potent New Tool," 137 Farm Chemicals 36 (Dec., 1974); Paul J. Carey, "Applying Agricultural Chemicals Through Sprinkler Irrigation Systems," 142 Agrichemical Age 8 (Feb., 1971). This consists of drenching either plant and soil or just the soil with a solution of the herbicidal composition at a time when the plants' root systems are sufficiently mature to take up the antidote. Application at an earlier stage, such as pre-plant, results in loss of activity of the antidote prior to development of the plants' receptivity.

Testing

The compositions and methods of this invention were tested in the following manner.

The thiocarbamate herbicides can be prepared by the procedures described in U.S. Pat. Nos. 2,913,327, 2,913,324, 3,185,720, and 3,198,786. The acetanilide herbicides were prepared by the procedures described in U.S. Pat. Nos. 3,442,945, 3,937,730, 3,780,090, and 2,863,752.

Stock solutions of each herbicide were prepared by weighing out the equivalent of 222 milligrams (mg) of active ingredient of the emulsifiable concentrate formulation and suspending it in 100 milliliters (ml) of water.

Ten ml of the solution were pipetted into a separate flask and diluted with water to 400 ml. This 400 ml solution, when applied to a flat, was equivalent to an application rate of 6 pounds per acre (lb/A). Solutions for application rates of 4 and 3 lb/A were made by adding 6.67 and 5.00 ml of stock solution to 400 ml portions of water.

Stock solutions of sodium azide were prepared by weighing out 222 mg of crystalline sodium azide and dissolving it in 100 ml of water.

Ten ml of the azide stock solution were removed with a pipette and diluted with water to a volume of 400 ml. This solution applied to a flat was equivalent to an application rate of 6 lb/A. Solutions for application rates corresponding to 2, 1, 0.50, and 0.25 lb/A were prepared by diluting 3.34, 1.67, 0.88 and 0.44 ml of stock solution in 400 ml portions of water.

On the day before seeding, aluminum flats, measuring 6.5×8.5×2.75 inches (16.5×21.59×7 cm) were filled to a depth of two inches with loamy sand soil treated with 50 parts per million (ppm) each of cis-N[(trichloromethyl)thio]-4-cyclohexane-1,2-dicarboximide, a fungicide sold as Captan®, and an 18—18—18 fertilizer, which contains 18% by weight equivalent each of nitrogen, phosphorus pentoxide, and potassium oxide.

After seeding flats were placed on greenhouse benches where temperature was maintained between 70° and 90° F. The flats were watered by sprinkling as needed to assure good plant growth.

TEST 1

The superiority of sodium azide over growth regulators was demonstrated in the following manner.

Two rows each of three hybrids of corn seeds were planted one inch deep with 20 seeds per flat. Nine days later, after seed germination, establishment of the root system, and growth to the two-leaf stage, the flats were drenched with the herbicide S-ethyl N,N-dipropylthiocarbamate and one of a variety of enzyme or growth regulators.

The results are shown in Table I.

TABLE I

| Antidotal Effectiveness of Various Compounds | | | | | |
|---|---|---|---|---|---|
| Herbicide Rate (lb/A) | Additive | | % of Corn Plants with Stem-twisting Injury | | |
| | Name | Rate (lb/A) | Days After Treatment | | |
| | | | 5 | 12 | 20 |
| none | none | | 0 | 0 | 0 |
| 3.00 | none | | 35 | 100 | 100 |
| 3.00 | sodium azide | 2.00 | 0 | 0 | 0 |
| 3.00 | 2,4-dichlorophen-oxyacetic acid | 2.00 | 0 | 30 | 60 |
| 3.00 | 2,3,5-triiodobenzoic acid | 10.00 | —¹ | 25 | 55 |
| 3.00 | 1-naphthaleneacetic acid | 10.00 | 5 | 15 | 50 |
| 3.00 | 3-[2-(3,5-dimethyl-2-oxocyclohexyl)-2-hydroxyethyl] glutarimide | 1.00 | —¹ | 5 | 15 |

¹Data unavailable.

TEST 2

This test involved a retest of the antidotally most effective compounds at lower rates, and with the herbicide S-ethyl N,N-dipropylthiocarbamate at the same and higher rates. The results are shown in Table II.

TABLE II

Antidotal Effectiveness of Sodium Salts

| Herbicide Rate (lb/A) | Additive Name | Rate (lb/A) | % of Corn Plants With Stem-twisting Injury Days After Treatment | | |
|---|---|---|---|---|---|
| | | | 5 | 13 | 20 |
| none | none | 0 | 0 | 0 | 0 |
| 3.00 | none | 0 | 45 | 100 | 100 |
| 6.00 | none | 0 | 60 | 100 | 100 |
| none | sodium azide | 2.00 | 0 | 0 | 0 |
| 3.00 | sodium azide | 2.00 | 0 | 0 | 0 |
| 3.00 | sodium azide | 1.00 | 0 | 5 | 10 |
| 3.00 | sodium azide | 0.50 | 0 | 10 | 20 |
| 3.00 | sodium azide | 0.25 | 40 | 100 | 100 |
| 6.00 | sodium azide | 2.00 | 0 | 0 | 5 |
| 6.00 | sodium azide | 1.00 | 0 | 15 | 20 |
| 6.00 | sodium azide | 0.50 | 0 | 35 | 55 |

TEST 3

The antidotal effectiveness of the compositions and method of this invention for the protection of three different corn hybrids from thiocarbamate and acetanilide herbicidal injury were tested in the following manner.

Five seeds of each hybrid were planted per row at a depth of one inch (2.54 cm) in each flat. Seven days later the herbicide and sodium azide were added to the soil. Flats were separately treated with stock solutions of each herbicide at a rate of 6 lb/A (6.72 kilograms per hectare k/ha) and with stock solutions of sodium azide at 2 and 6 lb/A (2.24 and 6.72 k/ha). These flats comprised the control groups.

The test flats were herbigated with each herbicide at 6 lb/A (6.72 k/ha) and sodium azide at either 2 or 6 lb/A (2.24 or 6.72 k/ha). Thirty corn plants or two flats were treated with each composition at the various rates.

Injury ratings were based on visual comparisons of test and control flats to the crops in untreated flats. The percentages of leaf-rolling and stem-twisting injuries were recorded at 8, 14, and 21 day intervals after herbigation. The percentage of stunting injury were measured 21 days after herbigation. The results appear in Table III.

TABLE III

Antidotal Effectiveness for Corn

| Herbicide | Sodium Azide Rate | Type of Injury | | | |
|---|---|---|---|---|---|
| | | % Leaf Roll or Stem Twist Days After Treatment | | | % Stunting at |
| Rate - 6 lb/A | lb/A | 8 | 14 | 21 | 21 Days |
| (none) | 2.00 | 0 | 0 | 0 | +40[1] |
| | 6.00 | 0 | 0 | 0 | +30 |
| 2-chloro-2',6'-diethyl- | none | 67 | 40 | 33 | 20 |
| N(methoxymethyl) | 2.00 | 0 | 0 | 0 | +40 |
| acetanilide | 6.00 | 0 | 0 | 0 | 10 |
| 2-ethyl-6-methyl-N— | none | 33 | 30 | 13 | +10 |
| (1'-methoxyprop-2'-yl) | 2.00 | 0 | 0 | 0 | +20 |
| N—chloroacetanilide | 6.00 | 7 | 3 | 0 | 10 |
| 2-chloro-N—Propyl | none | 0 | 0 | 0 | +50 |
| acetanilide | 2.00 | 0 | 0 | 0 | +70 |
| | 6.00 | 0 | 0 | 0 | 10 |
| S—ethyl-N,N— | none | 100 | 100 | 100 | 80 |
| dipropyl- | 2.00 | 0 | 17 | 60 | 20 |
| thiocarbamate | 6.00 | 0 | 0 | 30 | 30 |
| S—propyl N,N— | none | 90 | 100 | 100 | 80 |
| dipropyl- | 2.00 | 0 | 30 | 70 | 30 |
| thiocarbamate | 6.00 | 0 | 3 | 30 | 40 |
| S—ethyl N,N— | none | 63 | 63 | 70 | 10 |
| diisobutyl- | 2.00 | 0 | 0 | 0 | +40 |
| thiocarbamate | 6.00 | 0 | 0 | 0 | +50 |
| S—ethyl N—ethyl- | none | 57 | 70 | 77 | 10 |
| N—cyclo- | 2.00 | 0 | 0 | 0 | +30 |
| hexythiocarbamate | 6.00 | 0 | 0 | 0 | 0 |
| S—ethyl hexahydro- | none | 97 | 100 | 100 | 80 |
| 1H—azepine- | 2.00 | 0 | 0 | 10 | +30 |
| 1-carbothioate | 6.00 | 0 | 3 | 13 | 20 |

[1] "+" indicated % increase in growth over untreated growth rate.

TEST 4

There were three tests each conducted in the same manner as Test 3 to determine the antidotal effectiveness of sodium azide for the protection of soybeans from thiocarbamate herbicidal injury. The flats were herbigated seven days after seeding. Injury ratings were taken 20 days later. The results are summarized in Table IV.

TABLE IV

Antidotal Effectiveness for Soybeans

| Herbicide | | | % Injury | | | | | |
|---|---|---|---|---|---|---|---|---|
| | Rate | Sodium azide | Crinkled Leaves | | | Stunting | | |
| Name | (lb/A) | (lb/A) | Test 1 | Test 2 | Test 3 | Test 1 | Test 2 | Test 3 |
| Control Data: | | | | | | | | |
| none | | none | 0 | 0 | 0 | 0 | 0 | 0 |
| S—propyl N,N—dipropyl | 3.00 | none | 50 | 70 | 60 | 20 | 30 | 20 |
| thiocarbamate | 6.00 | none | 100 | 87 | 87 | 50 | 30 | 40 |
| S—methyl-N,N—dipropyl | 3.00 | none | — | 100 | 100 | — | 70 | 80 |
| thiocarbamate | | | | | | | | |
| Test Data: | | | | | | | | |
| S—propyl N,N—dipropyl | 3.00 | 1.00 | 28 | — | — | 5 | — | — |
| thiocarbamate | 3.00 | 3.00 | 7 | 0 | — | 10 | 40 | — |
| | 4.00 | 1.00 | — | — | 12 | — | — | 0 |
| | 4.00 | 2.00 | — | — | 10 | — | — | 0 |
| | 6.00 | 1.00 | — | — | 20 | — | — | 20 |
| | 6.00 | 2.00 | — | — | 0 | — | — | 10 |
| | 6.00 | 3.00 | 0 | 8 | — | 20 | 30 | — |
| S—ethyl-N,N—dipropyl | 3.00 | 1.00 | — | — | 100 | — | — | 60 |
| thiocarbamate | 3.00 | 2.00 | — | — | 100 | — | — | 40 |
| | 3.00 | 3.00 | — | 42 | — | — | 60 | — |

— = species not tested at the rate indicated

TEST 5

This test demonstrates the antidotal effectiveness of sodium azide for the protection of wheat, barley, and milo. Two rows of each crop species were planted 0.5 inches deep in a flat. The azide was combined with S-propyldipropylthiocarbamate and applied to the seven day old plants and soil by herbigation. Injury ratings were taken 17 days later. The results of this test appear in Table V.

TABLE V

| Antidotal Effectiveness for Wheat, Barley, Milo | | | | |
|---|---|---|---|---|
| Herbicide* | Sodium Azide | | % Stunting | |
| (lb/A) | (lb/A) | Wheat | Barley | Milo |
| 0.50 | — | 50 | 30 | 70 |
| 0.50 | 1.00 | 10 | 20 | 10 |
| 1.00 | — | 50 | 20 | 80 |
| 1.00 | 2.00 | 60 | 20 | 30 |
| 2.00 | — | 60 | 50 | 90 |
| 2.00 | 2.00 | 50 | 55 | 70 |

*S—propyl dipropylthiocarabamate

TEST 6

The purpose of this test was to verify the herbicidal effectiveness on weeds of compositions comprised of a thiocarbamate or acetanilide herbicide and sodium azide.

Six flats were seeded with one row each of two hybrids of corn, watergrass (*Echinochloa crusgalli*), foxtail (*Setaria viridis*), wild oat (*Avena fatua*), Johnsongrass (*Sorghum halepense*), and shattercane (*Sorghum bicolor*).

Five flats were planted with two rows of soybeans and one row of the above named weed species. Seeds were planted in furrows ½ inch deep and 6 inches long.

Seven days after planting they were herbigated as in the previous tests. Injury ratings were taken nine days later. Injuries were defined as stem-twisting for corn and leaf-crinkling for soybeans. Weed injury is the reduction in growth. The results appear in Table VI.

TABLE VI

| Herbicide | | Herbicidal Effectiveness | | | | | | |
|---|---|---|---|---|---|---|---|---|
| | | Sodium | | | % Injury | | | |
| Name | Rate (lb/A) | Azide (lb/A) | Corn #1 | Corn #2 | Water-grass | Fox-tail | Wild Oats | Shatter cane |
| S—ethyl-N,N—dipropyl | 0 | 0 | 0 | 0 | 0 | 0 | 0 | 0 |
| thiocarbamate | 0 | 0.50 | 0 | 0 | 0 | 0 | 0 | 0 |
| | 0 | 2.00 | 0 | 0 | 0 | 0 | 10 | 0 |
| | 3.00 | 0 | 100 | 100 | 60 | 70 | 60 | 60 |
| | 3.00 | 2.00 | 0 | 0 | 50 | 70 | 60 | 50 |
| N—(2'-methylcarbethoxy)- | 3.00 | 0 | 100 | 100 | 60 | 70 | 65 | 55 |
| 2,6-diethylchloroacetanilide | 3.00 | 2.00 | 20 | 17 | 60 | 75 | 60 | 60 |
| | | | Soybeans | | | | | |
| S—propyl N,N—dipropyl | 6.00 | 0 | 85 | | 70 | 60 | 60 | 60 |
| thiocarbamate | 6.00 | 0.50 | 66 | | 70 | 67 | 60 | 80 |

Test Results

A herbicidal composition comprised of a thiocarbamate or an acetanilide herbicide and a small amount of sodium azide retains the effectiveness of the herbicide on weeds while reducing crop injury. The herbicidal composition and its method of application are particularly effective for the control of weeds and the protection of corn. It is also effective for the protection of soybeans when low rates of sodium azide are used. Higher rates proved injurious for soybeans. Milo was protected at low herbicidal rates, but wheat and barley were protected only where both the herbicide and sodium azide were kept at low rates.

Formulations

The compositions of this invention may be formulated in any manner in which herbicides are generally formulated.

The object of the formulation is to apply the compounds and compositions to the loci where control is desired by a convenient method. The "loci" may include soil, seeds, seedlings, and plant vegetation.

Formulation will generally contain several additives. Among these are some inert ingredients and diluent carriers such as organic solvents, water, oil and water, water in oil emulsions, carriers of dust and granules, and surface active, wetting, dispersing, and emulsifying agents.

Fertilizers, e.g., ammonium nitrate, urea and superphosphate, may also be added.

Aids to rooting and growth, e.g., compost, manure, humus, sand, etc., may likewise be added.

The formulations are commonly dusts, wettable powders, granules solutions or emulsifiable concentrates.

Dusts are free-flowing powder compositions containing the herbicidal compound impregnated on a particulate carrier. The particle size of the carrier is usually in the approximate range of 30 to 50 microns. Examples of suitable carrier are talc, bentonite, diatomaceous earth, and pyrophyllite. Anticaking and antistatic agents can be added, if desired. The composition generally contains up to 50% of active ingredient. Dust, like liquid compositions, can be applied by sprays or dusts from boom and hand sprayers or airplanes.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Wade Van Valkenburg, Pesticide Formulations (Marcel Dekker, Inc., N.Y., 1973) at pages 79-84.

Granules comprise the herbicidal composition impregnated on a particulate inert carrier have a particle size of about 1 to 2 millimeters in diameter. The granules can be made by spraying a solution of the active ingredient in a volatile solvent onto the granuler carrier.

Suitable carriers in preparation of granules include clay, vermiculite, sawdust, granular carbon, etc.

The herbicidal composition can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compositions of this invention are ideally applied to the soil by addition to irrigation water supplied to the field to be treated. This method of application permits the penetration of the compositions into the soil as the water is absorbed therein.

I claim:

1. In the method of controlling weeds in crops by applying to the soil in which crops have been planted
   (a) an herbicidally effective amount of thiocarbamate herbicide of the formula

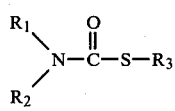

in which $R_1$ is selected from the group consisting of 1 to 6 carbon alkyl and 2 to 6 carbon alkenyl;

$R_2$ is selected from the group consisting of 1 to 6 carbon alkyl, 2 to 6 carbon alkenyl, cyclohexyl and phenyl; or $R_1$ and $R_2$ taken together with the nitrogen atom to which they are attached form hexahydro-1H-azepine; and $R_3$ is selected from the group consisting of 1 to 6 carbon alkyl, 1 to 6 carbon haloalkyl, 5 to 10 carbon alkylene alkylene ring, phenyl and benzyl; whereby the improvement consists in reducing the injury to said crop by employing (b) a non-phytotoxic antidotally effective amount of azide salt selected from the group consisting of alkali or alkaline earth elements or ammonium.

2. A method according to claim 1 where the alkali azide salt is sodium.

3. A method according to claim 1 or 2 in which $R_1$ and $R_2$ are each propyl and $R_3$ is ethyl.

4. A method according to claim 1 or 2 in which $R_1$, $R_2$, and $R_3$ are each propyl.

5. A method according to claim 1 or 2 in which $R_1$ and $R_2$ are each isobutyl and $R_3$ is ethyl.

6. A method according to claim 1 or 2 in which $R_1$ is ethyl, $R_2$ is cyclohexyl, and $R_3$ is ethyl.

7. A method according to claim 1 or 2 in which $R_1$ and $R_2$ together with the nitrogen atom to which they are attached form hexahydro-1H-azpeine, and $R_3$ is ethyl.

* * * * *